(12) United States Patent
Briscoe et al.

(10) Patent No.: US 6,984,516 B2
(45) Date of Patent: *Jan. 10, 2006

(54) MULTILAYERED MICROFLUIDIC DNA ANALYSIS SYSTEM AND METHOD

(75) Inventors: Cynthia G. Briscoe, Tempe, AZ (US); Huinan Yu, Chandler, AZ (US); Piotr Grodzinski, Chandler, AZ (US); Robert Marrero, Chandler, AZ (US); Jeremy W. Burdon, Scottsdale, AZ (US); Rong-Fong Huang, Tempe, AZ (US)

(73) Assignee: Motorola, Inc., Schaumburg, IL (US)

( * ) Notice: Subject to any disclaimer, the term of this patent is extended or adjusted under 35 U.S.C. 154(b) by 333 days.

This patent is subject to a terminal disclaimer.

(21) Appl. No.: 10/340,057

(22) Filed: Jan. 10, 2003

(65) Prior Publication Data

US 2003/0129646 A1    Jul. 10, 2003

Related U.S. Application Data

(60) Division of application No. 09/460,281, filed on Dec. 9, 1999, now Pat. No. 6,544,734, which is a continuation-in-part of application No. 09/337,086, filed on Jun. 21, 1999, now Pat. No. 6,572,830, which is a continuation-in-part of application No. 09/235,081, filed on Jan. 21, 1999, now Pat. No. 6,592,696.

(60) Provisional application No. 60/103,701, filed on Oct. 9, 1998.

(51) Int. Cl.
*C12M 1/34* (2006.01)
*C12P 19/34* (2006.01)
*B01J 19/08* (2006.01)

(52) U.S. Cl. .................. 435/287.2; 435/91.1; 435/91.2; 422/186.29

(58) Field of Classification Search ............... 435/91.1, 435/91.2, 287.2; 422/186.29
See application file for complete search history.

(56) References Cited

U.S. PATENT DOCUMENTS 5,587,128 A * 12/1996 Wilding et al. ............... 422/50
5,643,789 A *  7/1997 Ducheyne et al. .......... 435/402
6,544,734 B1 *  4/2003 Briscoe et al. ................ 435/6

\* cited by examiner

*Primary Examiner*—Bradley L. Sisson

(57) ABSTRACT

A multilayered microfluidic DNA analysis system includes a cell lysis chamber, a DNA separation chamber, a DNA amplification chamber, and a DNA detection system. The multilayered microfluidic DNA analysis system is provided as a substantially monolithic structure formed from a plurality of green-sheet layers sintered together. The substantially monolithic structure has defined therein a means for heating the DNA amplification chamber and a means for cooling the DNA amplification chamber. The means for heating and means for cooling operate to cycle the temperature of the DNA amplification chamber as required for performing a DNA amplification process, such as PCR.

29 Claims, 6 Drawing Sheets

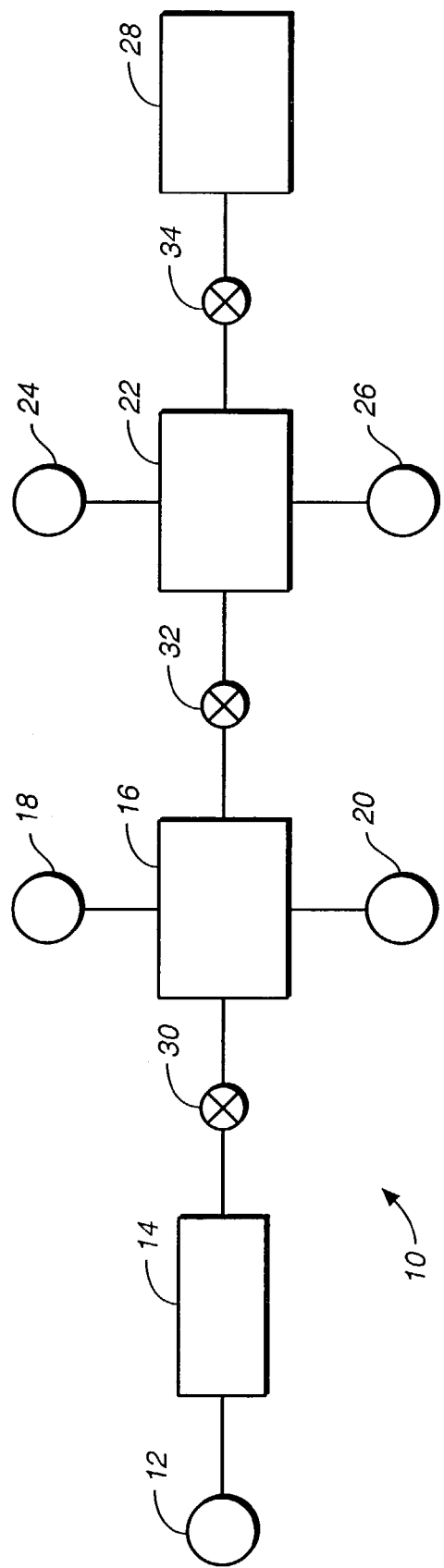
FIG._1

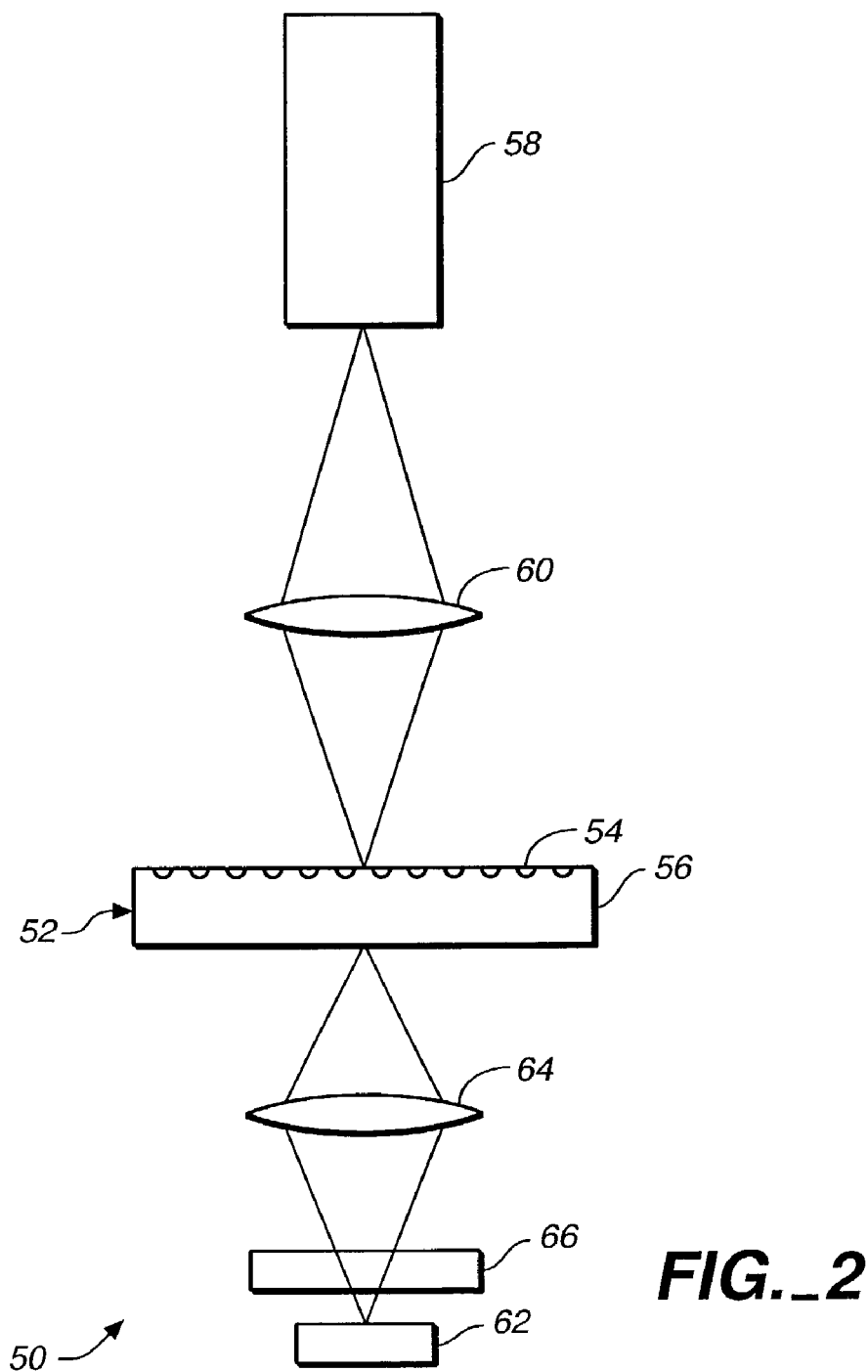
FIG._2

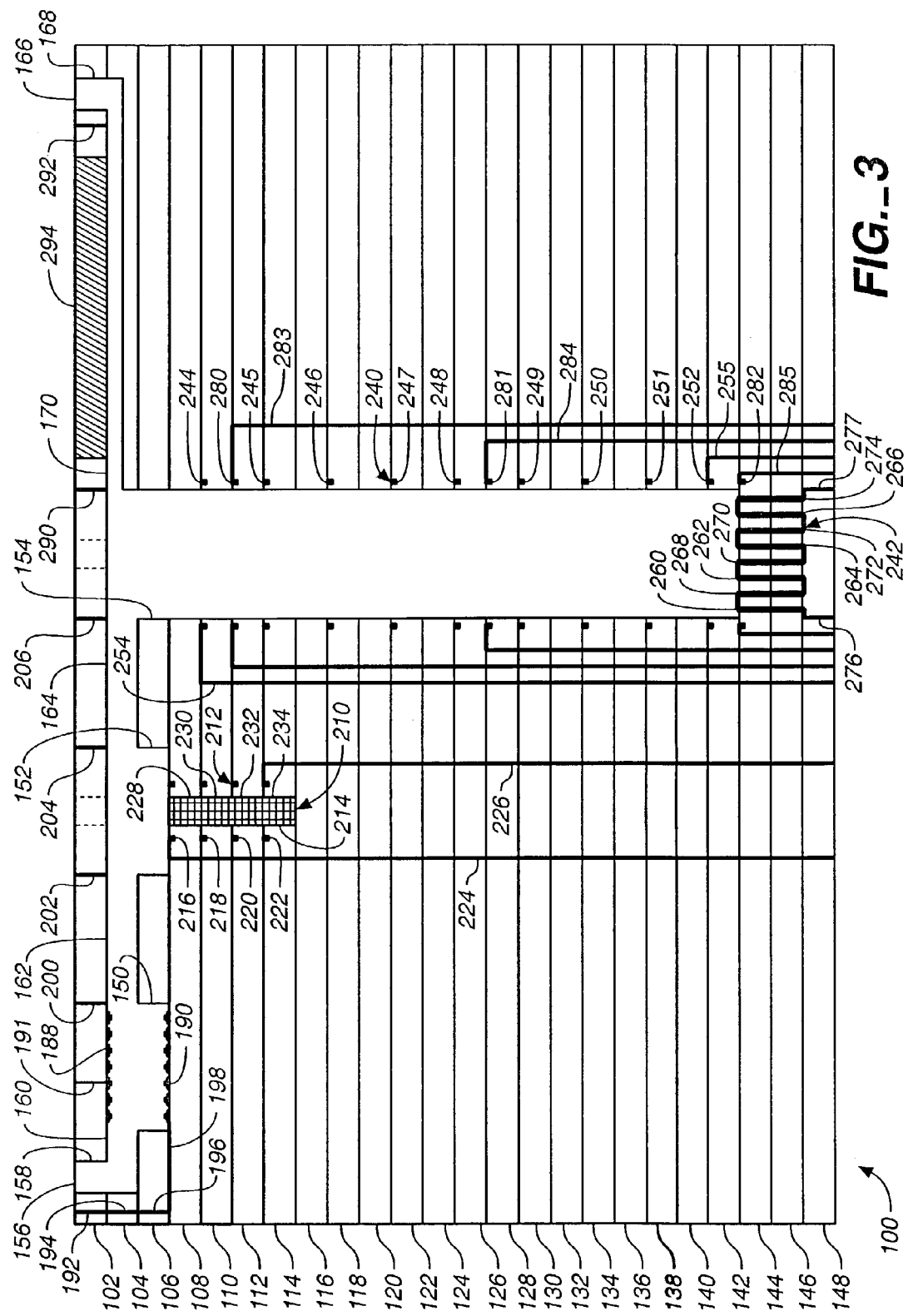
FIG._3

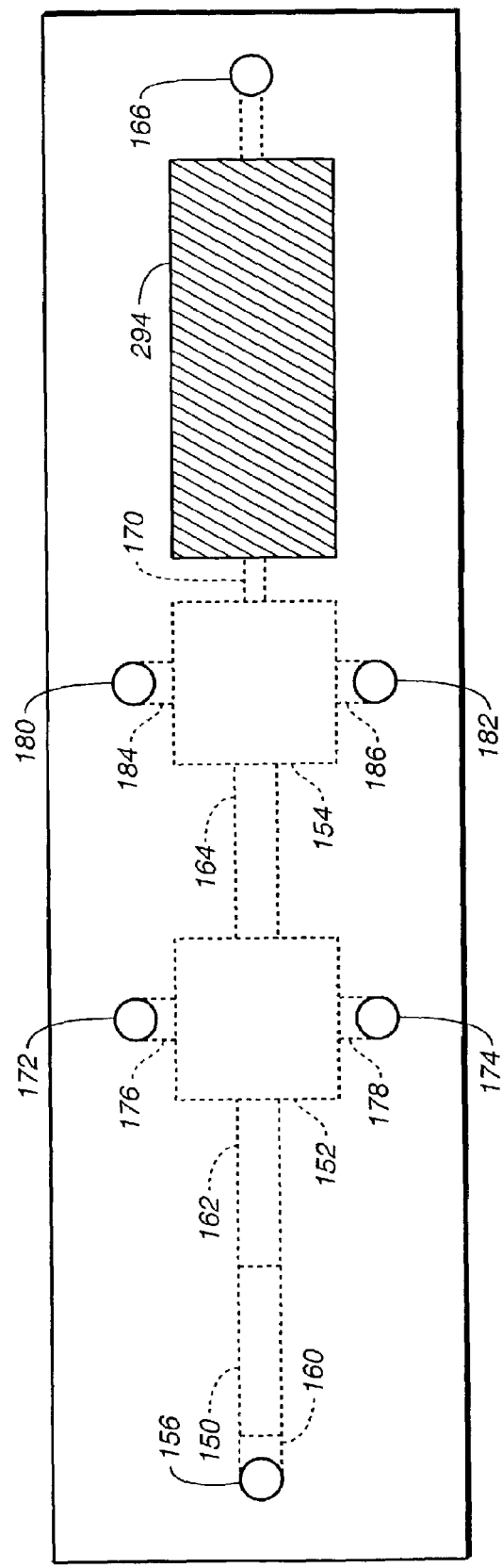
FIG._3A

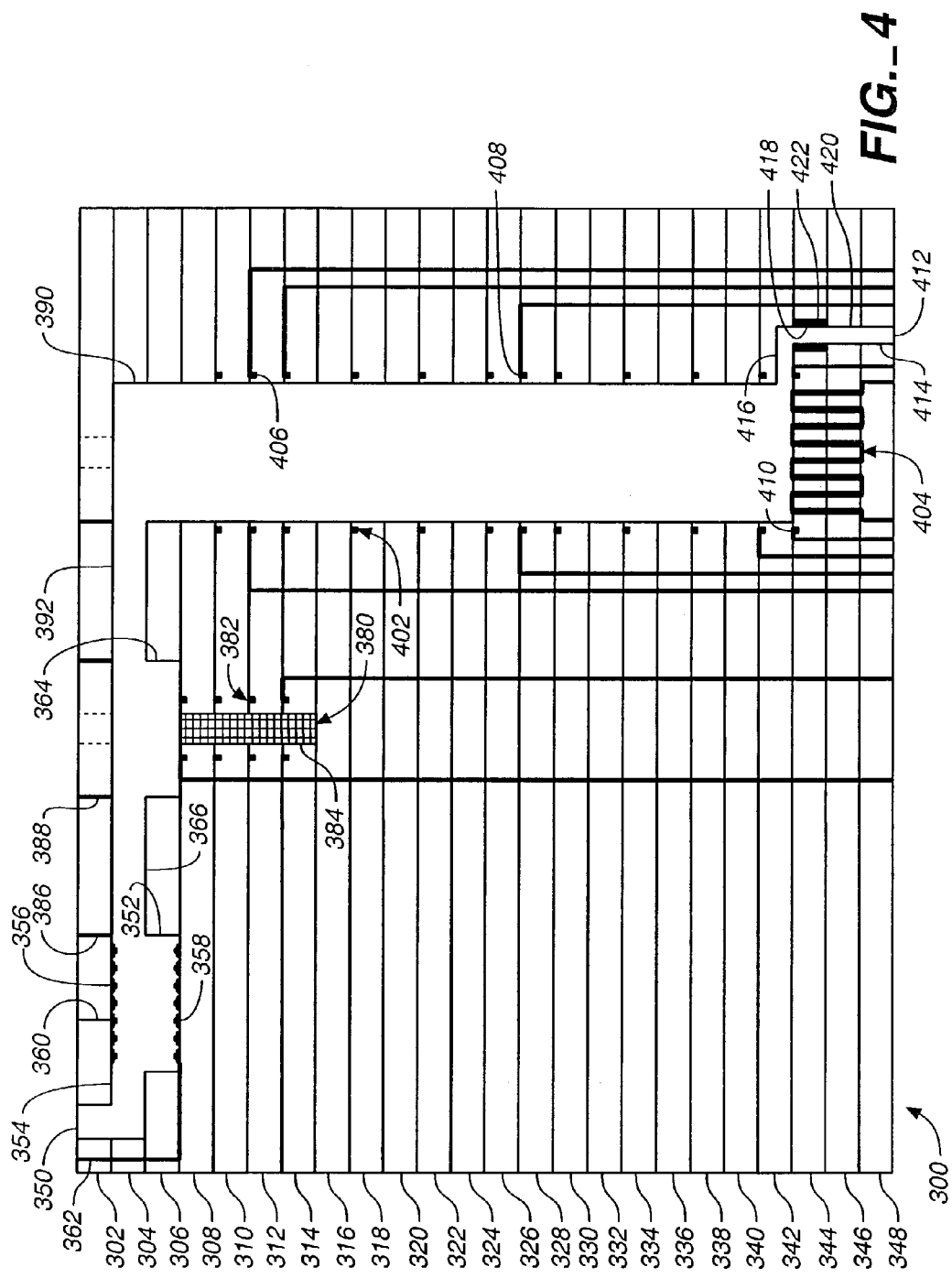
FIG._4

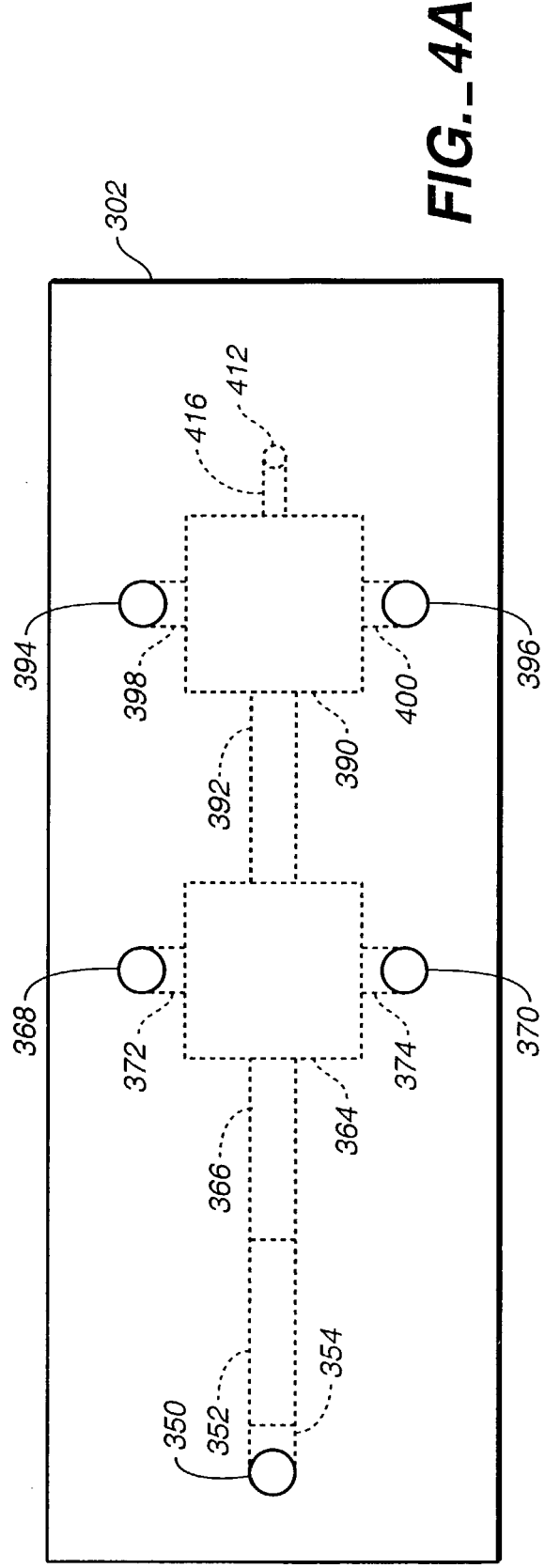
FIG._4A

MULTILAYERED MICROFLUIDIC DNA ANALYSIS SYSTEM AND METHOD

CROSS-REFERENCE TO RELATED APPLICATIONS

This application is a divisional of application U.S. Ser. No. 09/460,281, filed on Dec. 9, 1999, now U.S. Pat. No. 6,544,734, hereby incorporated by reference, which is a continuation-in-part of U.S. application Ser. No. 09/337,086, filed on Jun. 21, 1999, now U.S. Pat. No. 6,572,830, which is a continuation-in-part of U.S. application Ser. No. 09/235,081, filed on Jan. 21, 1999, now U.S. Pat. No. 6,592,696, which, in turn, claims the benefit of U.S. Provisional Application No. 60/103,701, filed Oct. 9, 1998. The disclosure of U.S. application Ser. No. 09/337,086 is fully incorporated herein by reference.

BACKGROUND OF THE INVENTION

1. Field of the Invention

This invention relates to the field of DNA amplification and analysis. More particularly, this invention relates to a system and method for releasing DNA from cells, for amplifying the DNA, and for detecting the amplified DNA products, wherein the device is formed from multiple layers of green-sheet that have been sintered together to form a substantially monolithic structure.

2. Description of Related Art

The conventional way of analyzing the DNA present in a sample of cells involves performing multiple steps using several different bench top instruments in a laboratory setting. First, the DNA must be extracted from the cells in the sample. This is typically done by performing any number of cell lysing procedures that cause the cells to break apart and release their contents. Next, the DNA is typically separated from the rest of the cell contents, as the presence of other cell contents may be undesirable in subsequent steps. To obtain an amount of DNA suitable for characterization, the DNA is amplified, such as by using the polymerase chain reaction (PCR). The resulting amplified DNA products can then be identified by any number of techniques.

The ability to perform all of these steps in a single miniaturized device has the potential for saving time and expense. Such miniaturized devices can be made much more portable than conventional apparatus, thereby enabling samples to be analyzed outside of the laboratory, such as the location where the samples are collected. A miniaturized DNA analysis device can also allow the analysis steps to be automated more easily. As a result, assays could be performed by less highly trained personnel than presently required.

Most efforts at fabricating miniaturized DNA analysis devices have focused on silicon as a substrate. For example a microchip device made out of silicon that performs the steps of cell lysis, PCR amplification, and electrophoretic analysis has been reported. See Larry C. Water, et al., "Microchip Device for Cell Lysis, Multiplex PCR Amplification, and Electrophoretic Sizing," *Anal. Chem.*, 70:158–162 (1998). Similarly, U.S. Pat. Nos. 5,639,423, 5,646,039, and 5,674,742 each disclose a microfabricated silicon device suited for performing PCR.

Silicon, however, suffers from a number of disadvantages as a substrate material. The cost of fabricating microfluidic devices in silicon can be relatively high. Silicon's high thermal conductivity can make the thermal cycling needed to perform PCR difficult, and silicon's property of being electrically semiconducting can hamper the operation of components that require the maintenance of a high potential difference. Most importantly, however, the difficulty of bonding multiple layers of silicon together makes it difficult to integrate complex components into the device.

SUMMARY OF THE INVENTION

In a first principal aspect, the present invention provides a multilayered microfluidic DNA amplification device comprising a substantially monolithic structure formed from a plurality of green-sheet layers sintered together. The green-sheet layers include particles selected from the group consisting of ceramic particles, glass particles, and glass-ceramic particles. The substantially monolithic structure has a fluid passageway defined, wherein the fluid passageway includes an inlet port for receiving fluid and a DNA amplification chamber for amplifying DNA in the fluid. The substantially monolithic structure also has defined therein a means for heating the DNA amplification chamber and a means for cooling the DNA amplification chamber.

In a second principal aspect, the present invention provides a DNA analysis system comprising a sample inlet port, a cell lysis chamber in fluid communication with the sample inlet port, a DNA separation chamber in fluid communication with said cell lysis chamber, a DNA amplification chamber in fluid communication with the DNA separation chamber, and a DNA detection system in fluid communication with the DNA amplification system. The DNA amplification chamber is defined by substantially monolithic structure that is formed from a plurality of green-sheet layers sintered together. The green-sheet layers contain particles selected from the group consisting of ceramic particles, glass particles, and glass-ceramic particles.

In a third principal aspect, the present invention provides a method for performing DNA analysis. A fluidic sample containing cells is placed in a cell lysis chamber. The cells in the cell lysis chamber are lysed to release cell contents, including sample DNA. The cell contents are passed to a DNA separation chamber. In the DNA separation chamber, the sample DNA is adsorbed onto a plurality of micro-beads and then eluted from the micro-beads. The sample DNA is passed to a DNA amplification chamber, where the sample DNA is amplified to produce amplified DNA. The amplified DNA is then detected. The cell lysis chamber, DNA separation chamber, and DNA amplification chamber are part of a fluid passageway defined in a substantially monolithic structure formed from a plurality of green-sheet layers sintered together. The green-sheet layers include particles selected from the group consisting of ceramic particles, glass particles, and glass-ceramic particles.

BRIEF DESCRIPTION OF THE DRAWINGS

FIG. 1 is a schematic diagram of a microfluidic DNA analysis system, in accordance with a preferred embodiment of the present invention.

FIG. 2 is a schematic diagram of the DNA detection system of FIG. 1, in accordance with a preferred embodiment of the present invention.

FIG. 3 is a cross-sectional sectional view of a microfluidic DNA amplification device, in accordance with a first preferred embodiment of the present invention.

FIG. 3A is a partial top plan view of the microfluidic DNA amplification device of FIG. 3, in accordance with a first preferred embodiment of the present invention.

FIG. 4 is a cross-sectional view of a microfluidic DNA amplification device, in accordance with a second preferred embodiment of the present invention.

FIG. 4A is a partial top plan view of the microfluidic DNA amplification device of FIG. 4, in accordance with a second preferred embodiment of the present invention.

DETAILED DESCRIPTION OF THE INVENTION

Shown schematically in FIG. 1 is a microfluidic DNA analysis system 10, in accordance with a preferred embodiment of the present invention. A sample inlet port 12 is in fluid communication with a cell lysis chamber 14, and cell lysis chamber 14 is in fluid communication with a DNA separation chamber 16. A buffer injection port 18 and a waste outlet port 20 are preferably provided in fluid communication with DNA separation chamber 16. A DNA amplification chamber 22 is in fluid communication with DNA separation chamber 16. A reagent injection port 24 and a waste outlet port 26 are preferably provided in fluid communication with DNA amplification chamber 22. Finally, a DNA detection system 28 is in fluid communication with DNA amplification chamber 22.

Preferably, a first fluid flow control system 30 is provided between cell lysis chamber 14 and DNA separation chamber 16 and a second fluid flow control system 32 is provided between DNA separation chamber 16 and DNA amplification chamber 22. A third fluid control system 34 may also be provided between DNA amplification chamber 22 and DNA detection system 28. Fluid flow control systems 30–34 serve to control the flow of fluid therethrough, thereby facilitating control over the flow of fluid through system 10, such as the flow of fluid from one chamber to another. Fluid flow control systems 30–34 can comprise microfluidic pumping systems, such as electroosmotic pumping systems. In particular, when an electroosmotic pumping system is provided as a pair of electrodes disposed in a microfluidic channel, little or no fluid flow occurs in the channel until the electroosmotic pumping system is turned on. Alternatively, fluid flow control systems 30–34 can comprise capillary stop valves. In the capillary stop valve approach, a discontinuity in the channel, such as an abrupt decrease in channel cross-section or the presence of a hydrophobic region, substantially prevents the passage of fluid until a sufficiently high pressure is applied.

In operation, DNA analysis system 10 extracts DNA from a small sample of cells, amplifies the extracted DNA, and then characterizes the amplified DNA, such as by detecting the presence of particular nucleotide sequences. Specifically, a fluidic sample containing the cells to be analyzed is introduced into system 10 through sample inlet port 12. From port 12, the sample enters cell lysis chamber 14. In chamber 14, the cells in the sample are lysed to release their cell contents, most notably the DNA contained in the cells. The cell lysis is preferably performed by subjecting the cells in chamber 14 to pulses of a high electric field strength, typically in the range of about 1 kV/cm to 10 kV/cm. However, other methods could also be used for cell lysis, such as chemical or thermal cell lysis.

After cell lysis, fluid flow control system 30 allows the fluid containing the cell contents to pass to DNA separation chamber 16. In chamber 16, the DNA from the cells is separated from the other cell contents. Preferably, the DNA separation is accomplished by manipulating paramagnetic micro-beads. Paramagnetic beads can be manipulated using magnetic fields, as the beads preferentially collect in areas of high magnetic field strength. Thus, the paramagnetic beads can be entrained in chamber 16 by the application of a magnetic field. However, when the magnetic field is turned off, the beads are able to move though the fluid in chamber 16.

The preferred paramagnetic beads have typical diameters in the range of 2.8 to 5 microns and preferentially adsorb duplex DNA under high salt (e.g., 3 to 4 molar $Na^+$) conditions. Suitable commercially available paramagnetic beads include Dynabeads DNA DIRECT™ from Dynal, Inc., Oslo, Norway and MPG borosilicate glass microbeads, product number MCPG0502, from CPG, Inc., Lincoln Park, N.J.

The paramagnetic beads are used to separate the DNA from the unwanted cell contents in the following way. First, fluid containing the paramagnetic beads is introduced into chamber 16, such as through buffer injection port 18. The amount of paramagnetic beads to be added will depend on the amount of DNA that is anticipated will be recovered from the sample and on the rated DNA loading capacity for the particular beads used. The beads are allowed to mix with the cell contents in chamber 16 for a few minutes. A magnetic field is then applied to chamber 16 to immobilize the paramagnetic beads. With the beads immobilized, the material in chamber 16 is exposed to a flow of a high salt buffer solution, typically about 3 to 4 molar $Na^+$, that is introduced through buffer injection port 18. In this flow, the buffer and unwanted cell contents are flushed out of chamber 16 through waste outlet port 20. However, under these high salt conditions, the DNA from the cells remains adsorbed on the surfaces of the paramagnetic beads. Moreover, during this high salt wash step, the paramagnetic beads are entrained in chamber 16 by the magnetic field.

After the high salt wash step, a low salt buffer, typically about 10 millimolar $Na^+$, is introduced into chamber 16 through buffer injection port 18. Under these low salt condition, the DNA elutes from the paramagnetic beads. With the paramagnetic beads entrained in chamber 16 by the use of the magnetic field, fluid flow control system 32 allows the low salt buffer containing the eluted DNA to pass to amplification chamber The DNA in chamber 22 is amplified, preferably by using the polymerase chain reaction (PCR). PCR is a well-known process whereby the amount of DNA can be amplified by factors in the range of $10^6$ to $10^8$. In the PCR process, the DNA is subjected to many cycles (typically about 20 to 40 cycles) of a specific temperature regimen, during which the DNA is exposed to a thermostable polymerase, such as AmpliTaq™ DNA polymerase from Perkin-Elmer, Inc., a mixture of deoxynucleoside triphosphates, and single-stranded oligonucleotide primers (typically about 15 to 25 bases in length). Each cycle comprises a thermal denaturation step, a primer annealing step, and a primer extension step. During the thermal denaturation step, double-stranded DNA is thermally converted to single-stranded DNA. The thermal denaturation step is typically performed at a temperature of 92 to 95° C. for 30 to 60 seconds. During the annealing step, the primers specifically anneal to portions of the single-stranded DNA. The annealing is typically performed at a temperature of 50 to 60° C. for about 30 seconds. During the primer extension step, the mononucleotides are incorporated into the annealed DNA in the 5' to 3' direction. The primer extension step is typically performed at 72° C. for 30 seconds to several minutes, depending on the characteristics of the nucleotide sequences that are involved. The result of each complete cycle is the generation of two exact copies of each original duplex DNA molecule.

The PCR process is conducted in chamber 22 to amplify the DNA introduced from chamber 16. Specifically, the polymerase and other reagents needed to perform PCR are added to chamber 22 through reagent injection port 24. The temperature of chamber 22 is adjusted to perform the various steps in the PCR process, as described above, for a desired number of cycles. Heating and cooling elements may be provided in thermal contact with chamber 22 for adjusting its temperature as required.

After PCR, fluid flow control system 34 allows the amplified DNA to pass to DNA detection system 28. DNA detection system 28 can include a capillary electrophoresis device, in which case the amplified products would be characterized by their electropheretic mobility. The DNA in the capillary electrophoresis device could be detected electrically at one or more locations along the electrophoresis channel. Preferably, however, the DNA is detected optically, such as by laser-induced fluorescence. For this approach, a fluorophore is added to chamber 22, such as through reagent injection port 24, and allowed to conjugate with the amplified DNA before the amplified DNA is introduced into the capillary electrophoresis device. An example of a suitable fluorophore is 1,1'-[1,3-propanediylbis[(dimethylimino-3,1-propanediyl]]bis[ 4-[(3-methyl-2(3H)-benzoxazolylidene) methyl]]-,tetraioide, which is sold under the name YOYO-1 by Molecular Probes, Inc., Eugene, Oreg.

Alternatively, DNA detection system 28 may include a molecular probe array, such as in DNA detection system 50 shown schematically in FIG. 2. System 50 includes a molecular probe array 52 comprising a plurality of test sites 54 formed into a substrate 56. Each one of test sites 54 contains known probe molecules, such as oligonucleotides, that are able to hybridize with a specific nucleotide sequence that may be present in the amplified DNA to which it is exposed. Preferably, the probe molecules are immobilized in a gel, such as a polyacrylamide gel, in each of test sites 54. By detecting in which one of test sites 54 hybridization occurs, the nucleotide sequences present in the amplified DNA can be determined. Detecting such hybridization can be accomplished by detecting changes in the optical or electrical properties of the test site in which hybridization occurs.

Preferably, hybridization is detected optically. To allow for optical detection, the amplified DNA is preferably conjugated to a fluorophore, such as YOYO-1 before being introduced to the molecular probe array, as described above. Then, a source 58 produces electromagnetic radiation at an excitation wavelength, i.e., a wavelength that induces fluorescence in the fluorophore, and a source optical system 60 focuses this electromagnetic radiation onto test sites 54. The fluorescence radiation from test sites 54 is then focused onto a detector 62 by means of a detector optical system 64. A filter 66 may be used to filter out the excitation wavelength. Further details regarding preferred optical detection systems is provided in co-pending U.S. patent application Ser. No. 09/440,031, entitled "System and Method for Detecting Molecules Using an Active Pixel Sensor," which was filed on Nov. 12, 1999. The disclosure of this co-pending patent application is fully incorporated herein by reference. Other types of molecular probe arrays could also be used, such as those described in U.S. Pat. No. 5,653,939, which is fully incorporated herein by reference.

DNA analysis system 10 is preferably provided as a substantially monolithic microfluidic device that is formed by laminating and sintering together multiple layers of green-sheet, as described in more detail below, though not all of system 10 may be provided on the same monolithic device. For example, DNA detection system 28 may be provided in whole, or in part, as a separate device. However, at least DNA amplification chamber 16 of system 10 is provided as a substantially monolithic microfluidic device.

In particular, shown in FIGS. 3 and 3A is a substantially monolithic microfluidic DNA amplification device 100, in accordance with a first preferred embodiment of the present invention. Shown in FIGS. 4 and 4A is a substantially monolithic microfluidic DNA amplification device 300, in accordance with a second preferred embodiment of the present invention. As described below in more detail, device 100 is provided with a capillary electrophoresis channel for DNA detection, and device 300 is intended to be coupled to a molecular probe array for DNA detection.

In accordance with the present invention, devices 100 and 300 are made from layers of green-sheet that have been laminated and sintered together to form a substantially monolithic structure. Green-sheet is a composite material that includes inorganic particles of glass, glass-ceramic, ceramic, or mixtures thereof, dispersed in a polymer binder, and may also include additives such as plasticizers and dispersants. The green-sheet is preferably in the form of sheets that are 50 to 250 microns thick. The ceramic particles are typically metal oxides, such as aluminum oxide or zirconium oxide. An example of such a green-sheet that includes glass-ceramic particles is "AX951" that is sold by E.I. Du Pont de Nemours and Company. An example of a green-sheet that includes aluminum oxide particles is "Ferro Alumina" that is sold by Ferro Corp. The composition of the green-sheet may also be custom formulated to meet particular applications. The green-sheet layers are laminated together and then fired to form a substantially monolithic multilayered structure. The manufacturing, processing, and applications of ceramic green-sheets are described generally in Richard E. Mistler, "Tape Casting: The Basic Process for Meeting the Needs of the Electronics Industry," Ceramic Bulletin, vol. 69, no. 6, pp. 1022–26 (1990), and in U.S. Pat. No. 3,991,029, which are incorporated herein by reference.

The method for fabricating devices 100 and 200 begins with providing sheets of green-sheet that are preferably 50 to 250 microns thick. The sheets of green-sheet are cut to the desired size, typically 6 inches by 6 inches for conventional processing. Each green-sheet layer may then be textured using various techniques to form desired structures, such as vias, channels, or cavities, in the finished multilayered structure.

Various techniques may be used to texture a green-sheet layer. For example, portions of a green-sheet layer may be punched out to form vias or channels. This operation may be accomplished using conventional multilayer ceramic punches, such as the Pacific Trinetics Corp. Model APS-8718 Automated Punch System. Instead of punching out part of the material, features, such as channels and wells may be embossed into the surface of the green-sheet by pressing the green-sheet against an embossing plate that has a negative image of the desired structure. Texturing may also be accomplished by laser tooling with a laser via system, such as the Pacific Trinetics LVS-3012.

Next, a wide variety of materials may be applied, preferably in the form of thick-film pastes, to each textured green-sheet layer. For example, electrically conductive pathways may be provided by depositing metal-containing thick-film pastes onto the green-sheet layers thick-film pastes typically include the desired material, which may be either a metal or a dielectric, in the form of a powder dispersed in an organic vehicle, and the pastes are designed to have the viscosity appropriate for the desired deposition technique, such as screen-printing. The organic vehicle may include resins, solvents, surfactants, and flow-control agents. The thick-film paste may also include a small amount of a flux, such as a glass frit, to facilitate sintering. Thick-film technology is further described in J. S. Provance, "Performance Review of Thick Film Materials," Insulation/Circuits (April, 1977) and in Morton L. Topfer, Thick Film Microelectronics, Fabrication, Design, and Applications (1977), pp, 41–59.

The porosity of the resulting thick-film can be adjusted by adjusting the amount of organic vehicle present in the thick-film paste. Specifically, the porosity of the thick-film can be increased by increased the percentage of organic vehicle in the thick-film paste. Similarly, the porosity of a green-sheet layer can be increased by increasing the proportion of organic binder. Another way of increasing porosity in thick-films and green-sheet layers is to disperse within the organic vehicle, or the organic binder, another organic phase that is not soluble in the organic vehicle. Polymer microspheres can be used advantageously for this purpose.

To add electrically conductive pathways, the thick film pastes typically include metal particles, such as silver, platinum, palladium, gold, copper, tungsten, nickel, tin, or alloys thereof. Silver pastes are preferred. Examples of suitable silver pastes are silver conductor composition numbers 7025 and 7713 sold by E. I. Du Pont de Nemours and Company.

The thick-film pastes are preferably applied to a green-sheet layer by screen-printing. In the screen-printing process, the thick-film paste is forced through a patterned silk screen so as to be deposited onto the green-sheet layer in a corresponding pattern. Typically, the silk screen pattern is created photographically by exposure to a mask. In this way, conductive traces may be applied to a surface of a green-sheet layer. Vias present in the green-sheet layer may also be filled with thick-film pastes. If filled with thick-filled pastes containing electrically conductive materials, the vias can serve to provide electrical connections between layers.

After the desired structures are formed in each layer of green-sheet, preferably a layer of adhesive is applied to either surface of the green-sheet. Preferably, the adhesive is a room-temperature adhesive. Such room-temperature adhesives have glass transition temperatures below room temperature, i.e., below about 20° C., so that they can bind substrates together at room temperature. Moreover, rather than undergoing a chemical change or chemically reacting with or dissolving components of the substrates, such room-temperature adhesives bind substrates together by penetrating into the surfaces of the substrates. Sometimes such room-temperature adhesives are referred to as "pressure-sensitive adhesives." Suitable room-temperature adhesives are typically supplied as water-based emulsions and are available from Rohm and Haas, Inc. and from Air Products, Inc. For example, a material sold by Air Products, Inc. as "Flexcryl 1653" has been found to work well.

The room-temperature adhesive may be applied to the green-sheet by conventional coating techniques. To facilitate coating, it is often desirable to dilute the supplied pressure-sensitive adhesive in water, depending on the coating technique used and on the viscosity and solids loading of the starting material. After coating, the room-temperature adhesive is allowed to dry. The dried thickness of the film of room-temperature adhesive is preferably in the range of 1 to 10 microns, and the thickness should be uniform over the entire surface of the green-sheet. Film thicknesses that exceed 15 microns are undesirable. With such thick films of adhesive voiding or delamination can occur during firing, due to the large quantity of organic material that must be removed. Films that are less than about 0.5 microns thick when dried are too thin because they provide insufficient adhesion between the layers.

From among conventional coating techniques, spin-coating and spraying are the preferred methods. If spin-coating is used, it is preferable to add 1 gram of deionized water for every 10 grams of "Flexcryl 1653." If spraying is used, a higher dilution level is preferred to facilitate ease of spraying. Additionally, when room-temperature adhesive is sprayed on, it is preferable to hold the green-sheet at an elevated temperature, e.g., about 60 to 70° C., so that the material dries nearly instantaneously as it is deposited onto the green-sheet. The instantaneous drying results in a more uniform and homogeneous film of adhesive.

After the room-temperature adhesive has been applied to the green-sheet layers, the layers are stacked together to form a multilayered green-sheet structure. Preferably, the layers are stacked in an alignment die, so as to maintain the desired registration between the structures of each layer. When an alignment die is used, alignment holes must be added to each green-sheet layer.

Typically, the stacking process alone is sufficient to bind the green-sheet layers together when a room-temperature adhesive is used. In other words, little or no pressure is required to bind the layers together. However, in order to effect a more secure binding of the layers, the layers are preferably laminated together after they are stacked.

The lamination process involves the application of pressure to the stacked layers. For example, in the conventional lamination process, a uniaxial pressure of about 1000 to 1500 psi is applied to the stacked green-sheet layers that is then followed by an application of an isostatic pressure of about 3000 to 5000 psi for about 10 to 15 minutes at an elevated temperature, such as 70° C. Adhesives do not need to be applied to bind the green-sheet layers together when the conventional lamination process is used.

However, pressures less than 2500 psi are preferable in order to achieve good control over the dimensions of such structures as internal or external cavities and channels. Even lower pressures are more desirable to allow the formation of larger structures, such as cavities and channels. For example, if a lamination pressure of 2500 psi is used, the size of well-formed internal cavities and channels is typically limited to no larger than roughly 20 microns. Accordingly, pressures less than 1000 psi are more preferred, as such pressures generally enable structures having sizes greater than about 100 microns to be formed with some measure of dimensional control. Pressures of less than 300 psi are even more preferred, as such pressures typically allow structures with sizes greater than 250 microns to be formed with some degree of dimensional control. Pressures less than 100 psi, which are referred to herein as "near-zero pressures," are most preferred, because at such pressures few limits exist on the size of internal and external cavities and channels that can be formed in the multilayered structure.

The pressure is preferably applied in the lamination process by means of a uniaxial press. Alternatively, pressures less than about 100 psi may be applied by hand.

As with semiconductor device fabrication, many devices may be present on each sheet. Accordingly, after lamination the multilayered structure may be diced using conventional green-sheet dicing or sawing apparatus to separate the individual devices. The high level of peel and shear resistance provided by the room-temperature adhesive results in the occurrence of very little edge delamination during the dicing process. If some layers become separated around the edges after dicing, the layers may be easily re-laminated by applying pressure to the affected edges by hand, without adversely affecting the rest of the device.

The final processing step is firing to convert the laminated multilayered green-sheet structure from its "green" state to form the finished, substantially monolithic, multilayered structure. The firing process occurs in two important stages as the temperature is raised. The first important stage is the binder burnout stage that occurs in the temperature range of about 250 to 500° C., during which the other organic materials, such as the binder in the green-sheet layers and the organic components in any applied thick-film pastes, are removed from the structure.

In the next important stage, the sintering stage, which occurs at a higher temperature, the inorganic particles sinter together so that the multilayered structure is densified and becomes substantially monolithic. The sintering temperature used depends on the nature of the inorganic particles present in the green-sheet. For many types of ceramics, appropriate sintering temperatures range from about 950 to about 1600° C., depending on the material. For example, for green-sheet containing aluminum oxide, sintering temperatures between 1400 and 1600° C. are typical. Other ceramic materials, such as silicon nitride, aluminum nitride, and silicon carbide, require higher sintering temperatures, namely 1700 to 2200° C. For green-sheet with glass-ceramic particles, a sintering temperature in the range of 750 to 950° C. is typical. Glass particles generally require sintering temperatures in the range of only about 350 to 700° C. Finally, metal particles may require sintering temperatures anywhere from 550 to 1700° C., depending on the metal.

Typically, the devices are fired for a period of about 4 hours to about 12 hours or more, depending on the material used. Generally, the firing should be of a sufficient duration so as to remove the organic materials from the structure and to completely sinter the inorganic particles. In particular, polymers are present as a binder in the green-sheet and in the room-temperature adhesive. The firing should be of sufficient temperature and duration to decompose these polymers and to allow for their removal from the multilayered structure.

Typically, the multilayered structure undergoes a reduction in volume during the firing process. During the binder burnout phase, a small volume reduction of about 0.5 to 1.5% is normally observed. At higher temperatures, during the sintering stage, a further volume reduction of about 14 to 17% is typically observed.

As noted above, preferably any dissimilar materials added to the green-sheet layers are co-fired with them. Such dissimilar materials could be added as thick-film pastes or as other green-sheet layers. The benefit of co-firing is that the added materials are sintered to the green-sheet layers and become integral to the substantially monolithic microfluidic device. However, to be co-fireable, the added materials should have sintering temperatures and volume changes due to firing that are matched with those of the green-sheet layers. Sintering temperatures are largely material-dependent, so that matching sintering temperatures simply requires proper selection of materials. For example, although silver is the preferred metal for providing electrically conductive pathways, if the green-sheet layers contain alumina particles, which require a sintering temperature in the range of 1400 to 1600° C., some other metal, such as platinum, must be used due to the relatively low melting point of silver (961° C.).

The volume change due to firing, on the other hand, can be controlled. In particular, to match volume changes in two materials, such as green-sheet and thick-film paste, one should match: (1) the particle sizes; and (2) the percentage of organic components, such as binders, which are removed during the firing process. Additionally, volume changes need not be matched exactly, but any mismatch will typically result in internal stresses in the device. But symmetrical processing, placing the identical material or structure on opposite sides of the device can, to some extent, compensate for shrinkage mismatched materials. Too great a mismatch in either sintering temperatures or volume changes may result in defects in or failure of some or all of the device. For example, the device may separate into its individual layers, or it may become warped or distorted.

Shown in FIGS. 3 and 3A is a DNA amplification device 100, in accordance with a first preferred embodiment of the present invention. Device 100 is made from green-sheet layers 102–148 that have been laminated and sintered together to form a substantially monolithic structure, as described above. Green-sheet layers 102–148 are each preferably about 100 microns thick. A cell lysis chamber 150 is formed into layers 104 and 106, a DNA separation chamber 152 is formed into layers 104 and 106, and a DNA amplification chamber 154 is formed into layers 104–142.

A sample inlet port 156 is defined by a via 158 formed into layer 102. Cell lysis chamber 150 is connected to via 158 through a channel 160 formed in layer 104. A channel 162 interconnecting chamber 150 with chamber 152 is formed in layer 104, and a channel 164 interconnects chamber 152 with chamber 154. An outlet port 166 is defined by a via 168 formed into layer 102, and a capillary electrophoresis channel 170 interconnects chamber 154 with via 168.

Cell lysis chamber 150 is typically about 50 microns wide, about 1 millimeter long, and extends about 100 microns below the channels that connect to it. DNA separation chamber 152 typically extends about 100 dimensions below the channels that connect to it, with a cross-section of 100 microns by 100 microns. DNA amplification chamber typically extends about 2 millimeters below the channels that connect to it, with a cross-section of roughly 1 millimeter by 1 millimeter. Channels 160, 162, and 164 are typically about 50 microns wide, 100 microns deep, and from about 500 microns to one centimeter long. Capillary electrophoresis channel 170 is typically about 45 microns wide, 20 microns wide, and from about 2 to 5 centimeters long.

As shown in FIG. 3A, a buffer injection port 172 is provided as a via formed into layer 102, and a waste outlet port 174 is provided as a via formed into layer 102. Ports 172 and 174 are connected to chamber 152 via channels 176 and 178, respectively, formed into layer 104. Similarly, a reagent injection port 180 is provided as a via formed into layer 102, and a waste outlet port 182 is provided as a via formed into layer 102. Channels 184 and 186, formed into layer 104, connect chamber 154 to ports 180 and 182, respectively.

As shown in FIG. 3, cell lysis chamber 150 is provided with opposing electrodes 188 and 190, which are sintered to layers 102 and 108, respectively. Electrode 188 is preferably formed by depositing, such as by screen printing, a conductive material in the form of a thick-film paste onto the lower surface of green-sheet layer 102. Similarly, electrode 190 is formed by depositing a conductive thick-film paste onto the upper surface of green-sheet layer 108. Electrodes 188 and 190 are preferably provided with a pointed surface for electric field enhancement. The pointed surfaces of electrodes 158 and 160 may be made by applying successive layers of conductive thick-film paste in a predetermined pattern.

Device 100 is provided with conductive leads to apply voltages to electrodes 188 and 190 from a voltage source (not shown) external to device 100. For example a conductor-filled via 191 may be provided in layer 102 to electrically connect electrode 188 to the outer surface of device 100. Similarly, a conductive lead defined by conductor-filled vias 192–196, formed into layers 102–106, and a conductive trace 198 formed on the surface of layer 108, electrically connects electrode 190 to the outer surface of device 100. To perform cell lysis, a voltage is applied between electrodes 158 and 160 sufficient to develop an electric field strength of about 10 to 50 kV/cm in cell lysis chamber 150. The voltage is preferably provided in the form of pulses at a frequency of about 10–100 Hz and a duty cycle of about 50%.

Channel 162 is preferably provided with electroosmotic pumping to transport fluid from chamber 150 to chamber 152. In fact, due to the small dimensions of channel 162, as compared to chamber 150, capillary forces prevent fluid in chamber 150 from flowing through channel 162 unless pressure or pumping is applied to the fluid. To enable electroosmotic pumping, electrodes 200 and 202 are disposed at opposite ends of channel 162, as shown in FIG. 3. Electrodes 200 and 202 may be conveniently provided as conductor-filled vias formed into layer 102. To enable electroosmotic pumping, a voltage is applied between electrodes 200 and 202, sufficient to develop an electric field strength of about 100 to 500 V/cm in channel 162.

Similarly, fluid is transported from chamber 152 to chamber 154 by electroosmotic pumping through channel 164. To allow for electroosmotic pumping, electrodes 204 and 206 are disposed at opposite ends of channel 164. A voltage is applied between electrodes 204 and 206, sufficient to develop an electric field strength of about 100 to 500 V/cm in channel 164. Electrodes 204 and 206 are preferably provided as conductor-filled vias in layer 102.

In order to use paramagnetic beads to separate the DNA from the lysed cell contents, as described above, device 100 is preferably provided with means for generating a magnetic field extending into DNA separation chamber 152. The magnetic field is preferably created by an electromagnet 210 that is integral to device 100. Electromagnet 210 preferably comprises a coil 212, with the axis of coil 212 extending into chamber 152, and a core 214 coaxial with coil 212. Coil 212 is preferably defined by loops 216–222 of conductive material sintered to layers 108–114, respectively, and a series of conductor-filled vias (not shown) formed into layers 108–112 that electrically connect loops 216–222. Loops 216–222 are preferably formed by depositing conductive material in the form of a thick-film paste onto green-sheet layers 108–114, respectively. To allow current to be applied to coil 212 from a current source (not shown) external to device 100, conductive leads 224 and 226 are provided. Conductive leads 224 and 226 may be disposed in device 100 in any convenient manner. For example, in the embodiment shown in FIG. 3, conductive lead 224 is defined by a trace of conductive material on the surface of layer 108 and a series of conductor-filled vias formed into layers 108–148, so as to provide an electrical connection from loop 216 to the exterior of device 100. Conductive lead 226 is defined by a trace of conductive material on the surface of layer 114 and a series of conductor-filled vias in layers 114–148, so as to provide and electrical connection from loop 222 to the exterior of device 100. Other configurations for leads 224 and 226 could be used, however.

Core 214 is made of a high magnetic permeability material, such as ferrite. Core 214 is preferably provided by forming aligned vias 228–234 in green-sheet layers 108–114 and filling vias 228–234 with a thick-film paste containing a ferrite material so that the ferrite material becomes sintered into layers 108–114. An example of a suitable ferrite-containing thick-film paste is SEI ferrite paste MPS #220, sold by Scrantom Engineering, Inc., Costa Mesa, Calif.

To bring the fluids in DNA amplification chamber 154 to the appropriate temperatures for performing PCR, device 100 is provided with a heater 240 and a cooling element 242 in thermal contact with chamber 154. Heater 240 is preferably configured as a coil surrounding chamber 154, the coil being defined by loops 244–252 of conductive material, preferably deposited in the form of a thick-film paste on the surface of and sintered to layers 110, 114, 118, 122, 126, 130, 132, 136, and 140, respectively. A series of conductor-filled vias (not shown) formed into layers 110–140 electrically connect loops 240–252.

To allow current to be applied to coil 240 from a current source (not shown) external to device 100, conductive leads 254 and 255 extend from loops 244 and 252, respectively, to the outer surface of device 100. To provide for efficient heating, loops 244–252 preferably have a high resistance compared to conductive leads 254 and 255. Conductive leads 254 and 255 may be disposed in device 100 in any convenient manner. For example, in the embodiment shown in FIG. 3, conductive lead 254 is defined by a trace of conductive material on the surface of layer 110 and a series of conductor-filled vias formed into layers 110–148. Conductive lead 255 is defined by a trace of conductive material on the surface of layer 142 and a series of conductor-filled vias in layers 142–148. Other configurations could be used for leads 254 and 255, however.

Cooling element 242 preferably cools chamber 154 thermoelectrically. Thermoelectric cooling element 242 may comprise alternating segments of n-type and p-type thermoelectric material, such as n-type segments 260–266 and p-type segments 268–274, that are connected in series by traces of conductive material, such as the conductive traces on the surfaces of layers 144 and 148, as shown in FIG. 3. In this way, when a voltage of the appropriate polarity is applied to thermoelectric element 242, it transfers heat from chamber 154 to layer 148. N-type segments 260–266 and p-type segments 268–274 may be provided by forming vias in green-sheet layers 144 and 146 and filling the vias with a thick-film paste containing either an n-type or p-type thermoelectric material, so that the thermoelectric material becomes sintered into layers 144 and 146. The thermoelectric material is preferably $Si_{0.8}Ge_{0.2}$ that has been doped, either with phosphorus to be n-type or with boron to be p-type. This material may be co-fired with the green-sheet layers at 850° C. in a reducing atmosphere.

To allow current to be applied to thermoelectric element 242 from a current source (not shown) external to device 100, conductive leads 276 and 277 extend from segments 260 and 274, respectively, to the outer surface of device 100. Conductive leads 276 and 277 may be disposed in device 100 in any convenient manner. For example, in the embodiment shown in FIG. 3, conductive leads 276 and 277 are each defined by a trace of conductive material on the surface of layer 148 and a conductor-filled via formed into layer 148.

An alternative approach for cooling DNA amplification chamber 154 is to reduce the thermal mass associated with chamber 154 and to rely on ambient cooling.

Device 100 also preferably includes at least one temperature sensor to measure the temperature of chamber 154. More particularly, because of the relatively large depth of chamber 154, the embodiment shown in FIG. 3 includes three temperature sensors 280, 281, and 282, disposed at three different vertical locations in thermal contact with chamber 154. In this way, an average measured temperature for chamber 154 can be calculated. Based on this average measured temperature, heater 240 and cooling element 242 can be controlled at each stage in the PCR process so that the chamber 154 is at the appropriate temperature.

Temperature sensors 280–282 each comprise a trace of a conductive material having a resistance that is substantially dependent on temperature. Platinum is the preferred conductive material. Temperature sensors 280–282 each comprise a platinum trace deposited as a thick-film paste on the surface of and sintered to green-sheet layers 112, 128, and 144, respectively. A pair of conductive leads 283–285 extend from each of temperature sensors 280–282 to the exterior of device 100, respectively. Conductive leads 283–285 may be disposed in device 100 in any convenient manner, such as by a series of conductive traces and conductor-filled vias.

Capillary electrophoresis channel 170 is used for electrophoretically separating the amplified DNA products from chamber 154. To be able to perform capillary electrophoresis, channel 170 is filled with an electrophoretic medium, such as a polyacrylamide gel, and electrodes 290 and 292 are disposed at opposite ends of channel 170. A voltage is applied between electrodes 260 and 262, sufficient to develop an electric field strength of about 100–500 V/cm. The applied electric field pumps fluid electroosmotically from chamber 154 into channel 170. Moreover, under the influence of this electric field, the amplified DNA products move through channel 170 toward outlet 166, and the different components in the amplified DNA products become separated based on their differing electrophoretic mobilities. Ports 182 and 166 maybe used for flushing out chamber 154 and channel 170.

Preferably the amplified DNA products are conjugated with a fluorophore, as described above, before entering channel 170, so that their location within channel 170 can be determined using laser-induced fluorescence. To perform laser-induced fluorescence, a window 294, made of an optically transmissive material, is provided in layer 102 over channel 170. Window 294 may be formed by punching out a portion of green-sheet layer 102 and then filling the punched-out portion with a thick-film paste containing glass particles. During the firing process, the glass in the thick-film paste becomes sintered to layer 102 so as to provide glass window 294 therein. Alternatively, green-sheet layer 102 may already contain glass particles so as to be optically transmissive when fired. Using either approach, optical access is provided to channel 170.

A light source (not shown), such as a laser, of a wavelength appropriate to induce fluorescence in the fluorophore-conjugated DNA products is focused through window 294 into channel 170. The fluorescence emitted from the fluorophore-conjugated DNA products is then imaged through window 294 onto a detector (not shown), such as a charge-coupled device.

As the fluids flowing through device 100 will contain DNA, it is important that all of the surfaces with which the fluid comes into contact be biocompatible. Layers 102–148 will themselves have varying degrees of biocompatibility, depending on the materials present in the green-sheet layers. However, it has been found that adequate biocompatibility can be achieved by coating the surfaces inside device 100 with poly-p-xylene.

Shown in FIGS. 4 and 4A is a DNA amplification device 300, in accordance with a second preferred embodiment of the present invention. Device 300 is similar to device 200 in most respects. In particular, device 300 is formed from green-sheet layers 302–348 that have been laminated and sintered together to form a substantially monolithic structure. Device 300 includes an inlet port 350 in fluid communication with a cell lysis chamber 352 via a channel 354. Cell lysis chamber 352 is provided with a pair of electrodes 356 and 358, with corresponding conductive leads 360 and 362, for performing electrostatic cell lysis. Cell lysis chamber 352 is connected to a DNA separation chamber 364 via a channel 366. A buffer injection port 368 and a waste outlet port are connected to DNA separation chamber 364 via channels 372 and 374, respectively. An electromagnet 380, having a coil of conductive material 382 and a core of high magnetic permeability material 384, is provided in device 300 to direct a magnetic field into DNA separation chamber 364. Channel 366 is provided with electrodes 386 and 388 for electroosmotic pumping. A DNA amplification chamber 390 is connected to DNA separation chamber 364 via a channel 392. A reagent injection port 394 and a waste outlet port 396 are connected to chamber 390 via channels 398 and 400, respectively. Device 300 is provided with a heater 402 for heating chamber 390 and a thermoelectric cooling element 404 for cooling chamber 390. Additionally, three temperature sensors 406, 408, and 410 are provided for measuring the temperature of chamber 390.

Unlike device 200, however, device 300 does not use capillary electrophoresis for DNA detection. Instead, device 300 is intended to be used with a molecular probe array, such as shown in FIG. 2 and described above. Specifically, device 300 is provided with an outlet port 412, to allow transfer of the amplified DNA products from device 300 to the molecular probe array. Outlet port 412 is defined by a via 414 formed into layer 348. A channel 416, formed into layer 442, and vias 418 and 420, formed into layers 344 and 346, along with via 414, define a fluid passageway from chamber 390 to outlet port 412.

Preferably, a capillary stop 422 is provided in the fluid passageway between chamber 390 and outlet port 412. In this way, during the PCR process conducted in chamber 390, fluid does not flow past capillary stop 422. However, if a sufficient pressure is applied to the fluid, it is able to flow through capillary stop 422 and exit device 300 through outlet port 412.

Capillary stop 422 may comprise a region of hydrophobic material formed into layer 344 surrounding via 418. The hydrophobic material can be a glass-ceramic material, preferably containing the humite mineral norbergite ($Mg_2SiO_4 \cdot MgF_2$) as a major crystal phase. This material is described in U.S. Pat. No. 4,118,237, which is incorporated herein by reference. Thick-film pastes containing particles of these hydrophobic glass-ceramic materials may be added to define capillary stop 422.

Although various embodiments of this invention have been shown and described, it should be understood that various modifications and substitutions, as well as rearrangements and combinations of the preceding embodiments, can be made by those skilled in the art, without departing from the novel spirit and scope of this invention.

We claim:

1. A multilayered microfluidic DNA amplification device comprising:
   a monolithic structure formed from a plurality of green-sheet layers sintered together, said green-sheet layers including particles selected from the group consisting of ceramic particles, glass particles, and glass-ceramic, particles;
   said monolithic structure having a fluid passageway defined therein, said fluid passageway including an inlet port for receiving fluid and a DNA amplification chamber for amplifying DNA in said fluid;

at least one fluid control system contiguous to the fluid passageway for providing electroosmotic pumping to transport the fluid therealong; and said monolithic structure having defined therein a means for heating said DNA amplification chamber and a means for cooling said DNA amplification chamber, said heating and cooling means subjecting the DNA to one or more cycles of a temperature regimen.

2. The multilayered microfluidic DNA amplification device of claim 1, wherein said means for heating includes a heater surrounding said DNA amplification chamber.

3. The multilayered microfluidic DNA amplification device of claim 2, wherein said heater is defined by an electrically conductive pathway, said electrically conductive pathway including a film portion formed by sintering a paste to at least one of said green-sheet layers.

4. The multilayered microfluidic DNA amplification device of claim 3, wherein said film portion includes a conductive trace sintered to one of said green-sheet layers, said conductive trace being formed by depositing said paste in a predetermined pattern onto a surface of said one of said green-sheet layers.

5. The multilayered microfluidic DNA amplification device of claim 3, wherein said film portion includes a conductor-filled via sintered to said one of said green-sheet layers, said conductor-filled via being formed by filling said paste into a via in said one of said green-sheet layers.

6. The multilayered microfluidic DNA amplification device of claim 1, wherein said means for cooling includes a thermoelectric element.

7. The multilayered microfluidic DNA amplification device of claim 6, wherein said thermoelectric element includes a thermoelectric via sintered to one of said green-sheet layers, said thermoelectric via being formed by filling a via in said one of said green-sheet layers with a paste containing a thermoelectric material.

8. The multilayered microfluidic DNA amplification device of claim 1, wherein said fluid passageway includes a cell lysis chamber.

9. The multilayered microfluidic DNA amplification device of claim 8, further comprising first and second electrodes disposed on opposing surfaces of said cell lysis chamber.

10. The multilayered microfluidic DNA amplification device of claim 9, wherein said first and second electrodes are defined by first and second traces of conductive material sintered to first and second green-sheet layers.

11. The multilayered microfluidic DNA amplification device of claim 1, wherein said fluid passageway includes a DNA separation chamber.

12. The multilayered microfluidic DNA amplification device of claim 11, wherein said monolithic structure has an electromagnet defined therein for directing a magnetic field into said DNA separation chamber.

13. The multilayered microfluidic DNA amplification device of claim 12, wherein said electromagnet includes a coil defined by an electrically conductive pathway, said electrically conductive pathway including a film portion formed by sintering a paste to at least one of said green-sheet layers.

14. The multilayered microfluidic DNA amplification device of claim 13, wherein said film portion includes a conductive trace sintered to one of said green-sheet layers, said conductive trace being formed by depositing said paste in a predetermined pattern onto a surface of said one of said green-sheet layers.

15. The multilayered microfluidic DNA amplification device of claim 13, wherein said film portion includes a conductor-filled via sintered to one of said green-sheet layers, said conductor-filled via being formed by filling said paste into a via in one of said green-sheet layers.

16. The multilayered microfluidic DNA amplification device of claim 12, wherein said electromagnet includes a core composed of a material having a magnetic permeability.

17. The multilayered microfluidic DNA amplification device of claim 16, wherein said core includes a film portion sintered to one of said green-sheet layers, said film portion being formed by filling a via in said one of green-sheet layers with a paste containing a magnetic permeability material.

18. The multilayered microfluidic DNA amplification device of claim 1, further comprising a temperature sensor for measuring the temperature of said DNA amplification chamber.

19. The multilayered microfluidic DNA amplification device of claim 18, wherein said temperature sensor comprises a material having a resistance dependent on temperature, said material being sintered to one of said green-sheet layers.

20. The multilayered microfluidic DNA amplification device of claim 1, wherein said fluid passageway includes a capillary electrophoresis channel.

21. The multilayered microfluidic DNA amplification device of claim 20, further comprising an electrode disposed in said capillary electrophoresis channel.

22. The multilayered microfluidic DNA amplification device of claim 21, wherein said electrode includes a film portion, said film portion being defined by a conductor-filled via sintered to one of said green-sheet layers, said conductor-filled via being formed by filling a paste into a via in said one of said green-sheet layers.

23. The multilayered microfluidic DNA amplification device of claim 20, further comprising a window providing optical access to said capillary electrophoresis channel.

24. The multilayered microfluidic DNA amplification device of claim 23, wherein said window is formed by sintering to one of said green-sheet layers a paste containing glass particles.

25. The multilayered microfluidic DNA amplification device of claim 1, wherein said fluid passageway includes an outlet port for releasing fluid, said outlet port being in fluid communication with said DNA amplification chamber.

26. The multilayered microfluidic DNA amplification device of claim 25, further comprising a capillary stop disposed in said fluid passageway between said DNA amplification chamber and said outlet port, whereby said capillary stop substantially blocks the flow of fluid at a first pressure but allows the flow of fluid at a second pressure.

27. The multilayered microfluidic DNA amplification device of claim 26, wherein said capillary stop comprises a hydrophobic region within said fluid passageway.

28. The multilayered microfluidic DNA amplification device of claim 27, wherein said hydrophobic region is formed by sintering a paste to at least one of said green-sheet layers, said paste containing particles of a hydrophobic glass-ceramic material.

29. A multilayered microfluidic DNA amplification device comprising:

a monolithic structure formed from a plurality of green-sheet layers sintered together, said green-sheet layers including particles selected from the group consisting of ceramic particles, glass particles, and glass-ceramic particles;

said monolithic structure having a fluid passageway defined therein, said fluid passageway including an inlet port for receiving the fluid, a cell lysis chamber for receiving the fluid from the inlet port, a DNA separation chamber, a buffer injection port and a first waste outlet port coupled to the DNA separation chamber, a DNA amplification chamber, a regent injection port and a second waste outlet port coupled to the DNA amplifification chamber, and a DNA detection chamber;

one or more electric field generation elements positioned in the cell lysis chamber;

a first fluid control system contiguous to the fluid passageway for providing electroosmotic pumping to transport the fluid from the cell lysis chamber to the DNA separation chamber;

a magnetic field element contiguous to the DNA separation chamber;

a second fluid control system contiguous to the fluid passageway for providing electroosmotic pumping to transport the fluid from the DNA seperation chamber to the DNA amplififcation chamber;

a heating and cooling element contiguous to the DNA amplification chamber for subjecting the DNA to a plurality of cycles of a temperature regimen;

a third fluid control system contiguous to the fluid passageway for providing electroosmotic pumping to transport the fluid from the DNA amplification chamber to the DNA detection chamber; and a transparent material positioned adjacent the DNA detection chamber allowing optical access thereto.

* * * * *